United States Patent
Ishihara et al.

(10) Patent No.: US 10,323,132 B2
(45) Date of Patent: Jun. 18, 2019

(54) POLYMER AND CROSSLINKED BODY THEREOF

(71) Applicants: THE UNIVERSITY OF TOKYO, Bunkyo-ku, Tokyo (JP); NOF CORPORATION, Shibuya-ku, Tokyo (JP)

(72) Inventors: Kazuhiko Ishihara, Tokyo (JP); Yuuki Inoue, Tokyo (JP); Kyoko Fukazawa, Tokyo (JP); Masaru Matsuda, Kawasaki (JP); Satoshi Yamada, Kawasaki (JP); Tomozumi Noda, Kawasaki (JP)

(73) Assignees: NOF Corporation, Tokyo (JP); The University of Tokyo, Tokyo (JP)

(*) Notice: Subject to any disclaimer, the term of this patent is extended or adjusted under 35 U.S.C. 154(b) by 163 days.

(21) Appl. No.: 15/554,803

(22) PCT Filed: Mar. 2, 2016

(86) PCT No.: PCT/JP2016/056407
§ 371 (c)(1),
(2) Date: Aug. 31, 2017

(87) PCT Pub. No.: WO2016/140259
PCT Pub. Date: Sep. 9, 2016

(65) Prior Publication Data
US 2018/0051140 A1 Feb. 22, 2018

(30) Foreign Application Priority Data
Mar. 3, 2015 (JP) .................................. 2015-041174

(51) Int. Cl.
| | | |
|---|---|---|
| *C09D 133/10* | (2006.01) | |
| *A61L 31/10* | (2006.01) | |
| *C08J 3/24* | (2006.01) | |
| *C08F 230/02* | (2006.01) | |
| *C09D 143/02* | (2006.01) | |
| *A61L 31/14* | (2006.01) | |
| *B05D 3/06* | (2006.01) | |
| *C08F 220/10* | (2006.01) | |
| *A61L 27/14* | (2006.01) | |
| *A61L 27/50* | (2006.01) | |

(52) U.S. Cl.
CPC .................. *C08J 3/24* (2013.01); *A61L 27/14* (2013.01); *A61L 27/50* (2013.01); *A61L 27/507* (2013.01); *A61L 31/10* (2013.01); *A61L 31/14* (2013.01); *B05D 3/06* (2013.01); *C08F 220/10* (2013.01); *C08F 230/02* (2013.01); *C09D 133/10* (2013.01); *C09D 143/02* (2013.01); *A61L 2430/20* (2013.01); *C08F 2800/10* (2013.01); *C08F 2800/20* (2013.01); *C08J 2343/02* (2013.01)

(58) Field of Classification Search
CPC ........ C09D 133/10; C09D 143/02; C08J 3/24; C08J 2343/02; C08F 230/02; C08F 220/10; B05D 3/06; A61L 31/14; A61L 31/10; A61L 2340/20; A61L 27/507; A61L 27/50; A61L 27/14
See application file for complete search history.

(56) References Cited

U.S. PATENT DOCUMENTS

| | | | | |
|---|---|---|---|---|
| 6,090,901 A | * | 7/2000 | Bowers | ................. C08F 230/02 526/277 |
| 6,706,260 B1 | | 3/2004 | Tanaka et al. | |
| 6,858,673 B1 | | 2/2005 | Sakamoto et al. | |
| 9,539,371 B2 | * | 1/2017 | Wen | ..................... C09D 131/00 |
| 2005/0208093 A1 | | 9/2005 | Glauser et al. | |
| 2007/0207186 A1 | * | 9/2007 | Scanlon | ..................... A61F 2/07 424/424 |
| 2011/0039736 A1 | * | 2/2011 | Funaoka | ............ C12N 15/1006 506/32 |
| 2012/0059111 A1 | | 3/2012 | Sandhu et al. | |

(Continued)

FOREIGN PATENT DOCUMENTS

| | | |
|---|---|---|
| JP | 2002-212491 A | 7/2002 |
| JP | 2010-059346 | 3/2010 |

(Continued)

OTHER PUBLICATIONS

Goda et al. Photoinduced phospholipid polymer grafting on Parylene film: Advanced lubrication and antibiofouling properties. Colloids and Surfaces B: Biointerferfaces. vol. 54 (1), pp. 67-73 (2007) (Year: 2007).*

PCT International Search Report dated Aug. 16, 2016 in connection with PCT International Application No. PCT/JP2016/056407, 4 pages.

Written Opinion of the International Search Authority dated Aug. 16, 2016 in connection with PCT International Patent Application No. PCT/JP2016/056407, 4 pages.

*Primary Examiner* — Sanza L. McClendon
(74) *Attorney, Agent, or Firm* — Amster, Rothstein & Ebenstein LLP

(57) ABSTRACT

Provided are a copolymer having enough biocompatibility to be used in a medical material application, and a method of forming a crosslinked body, which involves modifying a substrate surface with the copolymer so that the surface may be biocompatible. More specifically, a protein adsorption-suppressing effect and a cell adhesion-suppressing effect, which are features of a phosphorylcholine group, are imparted to the substrate surface. It has been found that the object is achieved by a copolymer containing a phosphorylcholine constitutional unit, a hydrophobic constitutional unit, and a photoreactive constitutional unit at a specific ratio.

13 Claims, No Drawings

(56) References Cited

U.S. PATENT DOCUMENTS

| | | | |
|---|---|---|---|
| 2012/0258313 A1* | 10/2012 | Wen | C09D 131/00 |
| | | | 428/412 |
| 2013/0053470 A1 | 2/2013 | Raisin-Dadre et al. | |
| 2015/0328375 A1 | 11/2015 | Glauser et al. | |
| 2015/0359944 A1* | 12/2015 | Wen | C09D 131/00 |
| | | | 428/447 |
| 2015/0367290 A1* | 12/2015 | Nakashima | C09D 143/02 |
| | | | 210/506 |

FOREIGN PATENT DOCUMENTS

| | | |
|---|---|---|
| JP | 2010-059367 | 3/2010 |
| JP | 2012-46761 A | 3/2012 |
| JP | 2013-539399 A | 10/2013 |
| JP | 2014-520191 A | 8/2014 |
| WO | 00/01424 A1 | 1/2000 |

* cited by examiner

POLYMER AND CROSSLINKED BODY THEREOF

CROSS-REFERENCE TO RELATED APPLICATIONS

This application is a U.S. national stage entry under 35 U.S.C. § 371 of PCT International Patent Application No. PCT/JP2016/056407, filed Mar. 2, 2016, which claims priority to Japanese Patent Application No. 2015-041174, filed Mar. 3, 2015, the contents of which are incorporated by reference herein into the subject application.

TECHNICAL FIELD

The present invention relates to a polymer and a crosslinked body formed from the polymer.

The present application claims priority from Japanese Patent Application No. 2015-041174, which is incorporated herein by reference.

BACKGROUND ART

A phosphorylcholine group-containing polymer has excellent biocompatibility typified by blood compatibility. Accordingly, the phosphorylcholine group-containing polymer has been utilized in an application where a coating of the polymer is formed on the surface of a substrate poor in biocompatibility to make the surface biocompatible. Specifically, the polymer has been applied to surface treatment agents for various medical devices, such as an artificial heart, an artificial lung, an artificial vessel, and a contact lens (Non Patent Literature 1).

In such application, the polymer is often used as described below. The polymer is bonded to the substrate surface to which biocompatibility is to be imparted by physical bonding or chemical bonding to form a hydrous coating gel on the substrate surface. In order to perform the physical bonding on the substrate surface, for example, a method involving introducing a comonomer having a hydrophobic group into the polymer having a phosphorylcholine group to perform the physical bonding, or a method involving introducing an ionic group into the polymer to perform ionic bonding is used.

In each of those methods, however, part of the structure of the polymer needs to be substituted with another functional group, and hence the function of a phosphorylcholine group cannot be sufficiently exhibited. Further, when an affinity between the polymer and the substrate is insufficient, the durability of the coating becomes insufficient and hence the coating peels. Meanwhile, a phosphorylcholine group-containing polymer having introduced thereinto a chemical bonding group is chemically bonded to the substrate surface. Accordingly, even when the number of functional groups to be introduced is small, the polymer is bonded to the substrate and hence a coating having relatively high durability can be formed (Patent Literature 1). In this case, however, the presence of a functional group on the substrate surface is an indispensable condition. In addition, in general, bonding between molecules of the phosphorylcholine group-containing polymer does not occur, and hence the durability has not been sufficient. Further, the step of inactivating an unreacted functional group at the time of the chemical bonding through a posttreatment is also required, and hence the phosphorylcholine group-containing polymer having introduced thereinto a chemical bonding group has involved many problems in practical use.

In view of the foregoing, a phosphorylcholine group-containing polymer having photoreactivity has been proposed (Patent Literature 2). Even when a substrate having no chemical bonding functional group on its surface is selected, the polymer can be bonded to the surface of the substrate. In addition, the polymer is excellent in coating formability. However, the polymer has an azido group, and hence sufficient management is needed to secure safety at the time of its production and at the time of its transportation, and stability after the production. Therefore, the polymer has involved problems in terms of supply stability and scale-up property to be solved before its provision to the market.

Sufficient pursuits have not been made on a polymer that has a photoreactive group to be bonded to a substrate surface to be made biocompatible and that is used for forming, on the substrate surface to be made biocompatible, a stable crosslinked body for covering the substrate surface, and a crosslinked body thereof.

CITATION LIST

Patent Literature

[PTL 1] U.S. Pat. No. 6,090,901 A
[PTL 2] JP 2010-059367 A

Non Patent Literature

[NPL 1] Kazuhiko Ishihara, MMJ the Mainichi medical journal, "Medical Forest: Prospects for the Future (2): New Material for Medical Use "MPC Polymer"", 2010, Vol. 6, No. 2, p. 68-70

SUMMARY OF INVENTION

Technical Problem

A sufficient pursuit has not been made on a polymer that has a photoreactive group to be bonded to a substrate surface to be made biocompatible and that is used for forming a stable crosslinked body for covering the surface.

That is, an object of the present invention is to provide a polymer having enough biocompatibility to be used in a medical material application, and a method of forming a crosslinked body, which involves modifying a substrate surface with the polymer so that the surface may be biocompatible. More specifically, the object is to impart a protein adsorption-suppressing effect and a cell adhesion-suppressing effect, which are features of a phosphorylcholine group, to the substrate surface.

Solution to Problem

The inventors of the present invention have made extensive investigations in view of the object, and as a result, have found that the object is achieved by a copolymer containing a phosphorylcholine constitutional unit, a hydrophobic constitutional unit, and a photoreactive constitutional unit at a specific ratio. Thus, the inventors have completed the present invention.

That is, the present invention is as described below.

1. A copolymer, including constitutional units represented by the following formula (1a) to the following formula (1c), in which:

ratios a, b, and c of the respective constitutional units satisfy the following:

$a/(a+b+c)=0.30$ to $0.90$;

$b/(a+b+c)=0.01$ to $0.69$; and $c/(a+b+c)=0.01$ to $0.20$; and the copolymer has a weight-average molecular weight of from 10,000 to 1,000,000:

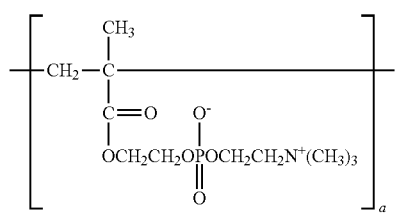
(1a)

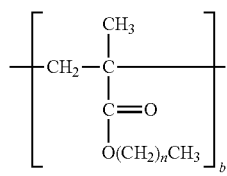
(1b)

where n represents from 3 to 17;

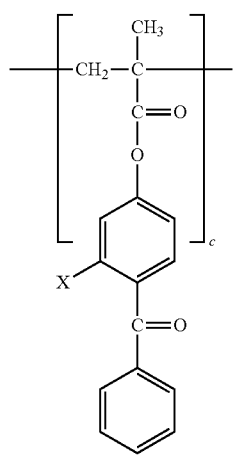
(1c)

where X represents —H or a —OH group.

2. A copolymer according to the above-mentioned item 1, in which the constitutional unit represented by the formula (1a) includes 2-methacryloyloxyethyl-2-trimethylammonioethyl phosphate, the constitutional unit represented by the formula (1b) includes butyl methacrylate, and the constitutional unit represented by the formula (1c) includes 4-methacryloyloxybenzophenone.

3. A copolymer according to the above-mentioned item 1, in which the constitutional unit represented by the formula (1a) includes 2-methacryloyloxyethyl-2-trimethylammonioethyl phosphate, the constitutional unit represented by the formula (1b) includes butyl methacrylate, and the constitutional unit represented by the formula (1c) includes 4-methacryloyloxy-2-hydroxybenzophenone.

4. A copolymer according to the above-mentioned item 1, in which the constitutional unit represented by the formula (1a) includes 2-methacryloyloxyethyl-2-trimethylammonioethyl phosphate, the constitutional unit represented by the formula (1b) includes stearyl methacrylate, and the constitutional unit represented by the formula (1c) includes 4-methacryloyloxybenzophenone.

5. A surface treatment agent, including the copolymer of any one of the above-mentioned items 1 to 4.

6. A surface treatment agent according to the above-mentioned item 5, in which the surface treatment agent includes a surface treatment agent for suppressing protein adsorption.

7. A surface treatment agent according to the above-mentioned item 5, in which the surface treatment agent includes a surface treatment agent for suppressing cell adhesion.

8. A method of forming a crosslinked body, including:
coating a substrate surface with the copolymer of any one of the above-mentioned items 1 to 4 or the surface treatment agent of any one of the above-mentioned items 5 to 7; and
then irradiating the substrate surface with light to form the crosslinked body on the substrate surface.

9. A crosslinked body, which is obtained by the method of forming a crosslinked body of the above-mentioned item 8.

10. A crosslinked body, which is obtained by irradiating the copolymer of any one of the above-mentioned items 1 to 4 or the surface treatment agent of any one of the above-mentioned items 5 to 7 with light.

11. A medical device, including the crosslinked body of the above-mentioned item 9 or 10.

12. An application for producing a surface treatment agent using a copolymer including constitutional units represented by the following formula (1a) to the following formula (1c), in which:
ratios a, b, and c of the respective constitutional units satisfy the following:

$a/(a+b+c)=0.30$ to $0.90$;

$b/(a+b+c)=0.01$ to $0.69$; and $c/(a+b+c)=0.01$ to $0.20$; and the copolymer has a weight-average molecular weight of from 10,000 to 1,000,000:

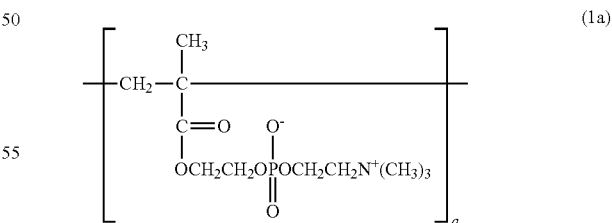
(1a)

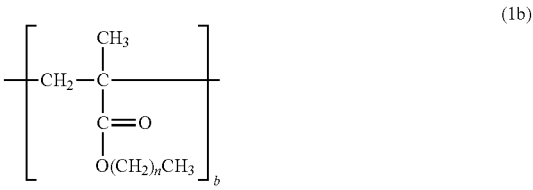
(1b)

where n represents from 3 to 17;

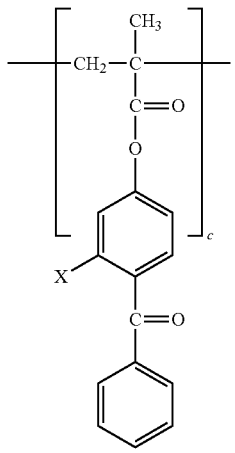

where X represents —H or a —OH group.

Advantageous Effects of Invention

When a substrate is coated with the polymer of the present invention and the substrate is irradiated with light, a biocompatible material in which the substrate is modified so as to be biocompatible can be provided.

DESCRIPTION OF EMBODIMENTS

The present invention is described in more detail below.

A copolymer serving as a subject matter of the present invention includes constitutional units represented by the following formula (1a) to the following formula (1c), in which: ratios a, b, and c of the respective constitutional units satisfy the following: $a/(a+b+c)=0.30$ to $0.90$; $b/(a+b+c)=0.01$ to $0.69$; and $c/(a+b+c)=0.01$ to $0.20$; and the copolymer has a weight-average molecular weight of from $10,000$ to $1,000,000$:

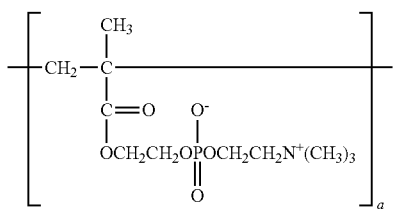

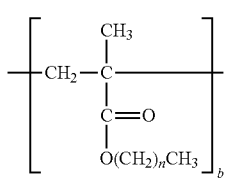

where n represents from 3 to 17;

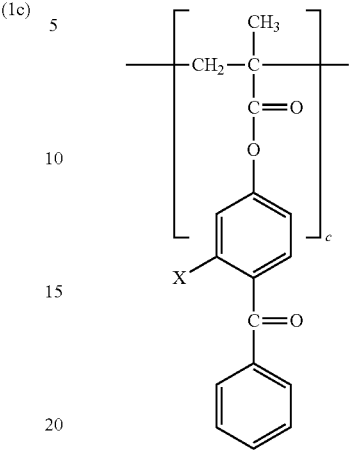

where X represents —H or a —OH group.

The copolymer of the present invention is a copolymer formed of a phosphorylcholine constitutional unit, a hydrophobic constitutional unit, and a photoreactive constitutional unit.

A surface treatment agent serving as a subject matter of the present invention includes the copolymer of the present invention.

A method of forming a crosslinked body serving as a subject matter of the present invention has a feature of including: coating a substrate surface with the copolymer of the present invention or the surface treatment agent of the present invention; and then irradiating the substrate surface with light to form the crosslinked body on the substrate surface.

A crosslinked body serving as a subject matter of the present invention is obtained by the method of forming a crosslinked body of the present invention, or is obtained by irradiating the copolymer of the present invention or the surface treatment agent of the present invention with light.

A medical device serving as a subject matter of the present invention includes the crosslinked body of the present invention.

The respective constitutional units of the copolymer of the present invention are described below.

[Phosphorylcholine Constitutional Unit]

The copolymer of the present invention contains, in its structure, a constitutional unit based on a phosphorylcholine (PC) group-containing monomer (see: 2a). In the structure of the copolymer, a phosphorylcholine group is a polar group having the same structure as that of a phospholipid serving as a main component of a biological membrane. The introduction of a phosphorylcholine group into the copolymer (polymer) can impart biocompatibility, such as a protein adsorption-suppressing effect, a cell adhesion-suppressing effect, antithrombogenicity, or hydrophilicity, to the polymer.

Further, when the polymer is subjected to a light treatment or the like on the surface of a substrate, biocompatibility can be imparted to the substrate.

An example of the PC group-containing monomer is 2-methacryloyloxyethyl-2'-(trimethylammonio)ethyl phosphate (see: 3a).

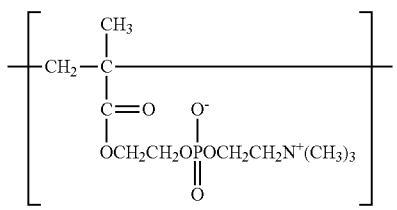

(2a)

[Hydrophobic Constitutional Unit]

The copolymer of the present invention contains, in its structure, a constitutional unit based on a hydrophobic group-containing monomer (see: 2b). When a hydrophobic group physically adsorbs to a hydrophobic substrate surface, the applicability of the polymer can be improved.

Examples of the hydrophobic group-containing monomer include, but are not particularly limited to, methacrylic acid esters each having a hydrophobic substituent, such as butyl methacrylate, hexyl methacrylate, 2-ethylhexyl methacrylate, decyl methacrylate, dodecyl methacrylate, tridecyl methacrylate, and stearyl methacrylate.

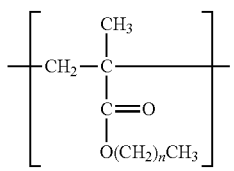

(2b)

(n=3 to 17)

[Photoreactive Constitutional Unit]

The copolymer of the present invention contains, in its structure, a constitutional unit based on a photoreactive benzophenone group-containing monomer (see: 2c). A benzophenone group is brought into a triplet excited state rich in reactivity by photoirradiation, and can be bonded to a substrate or a polymer by abstracting a hydrogen atom therefrom. Examples of the benzophenone group-containing monomer include, but are not particularly limited to, 4-methacryloyloxybenzophenone (MBP) and 4-methacryloyloxy-2-hydroxybenzophenone (MHP).

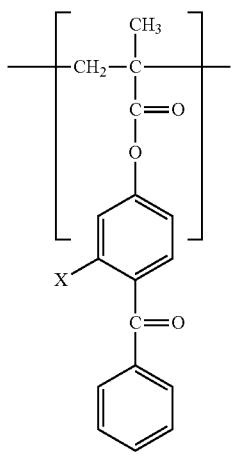

(2c)

X in the formula represents —H or a —OH group.

When the weight-average molecular weight of the copolymer of the present invention is less than 10,000, it is difficult to purify the polymer, and when the weight-average molecular weight is more than 1,000,000, viscosity at the time of its production becomes so high that it may be difficult to handle the copolymer.

In the formula (1a), the formula (1b), and the formula (1c), a, b, and c represent the ratios (constituent ratios) of the three constitutional units represented by the formulae (2a), (2b), and (2c), i.e., the molar ratios of the corresponding monomers.

Here, a, b, and c merely represent the ratios of the constitutional units, and do not mean that the polymer of the present invention is only a block polymer formed of a block represented by the formula (2a), a block represented by the formula (2b), and a block represented by the formula (2c). The polymer of the present invention may be a random copolymer in which the monomers represented by the formula (2a), the formula (2b), and the formula (2c) are randomly copolymerized, may be a block copolymer, or may be a copolymer in which a random moiety and a block moiety are mixed. In addition, an alternating copolymer moiety may be present.

In addition, the ratios a, b, and c representing the ratios of the constitutional units may be arbitrarily adjusted, and only need to be such that the polymer is soluble in an aqueous medium.

In addition, the ratios a, b, and c satisfy the following: $a/(a+b+c)=0.30$ to 0.90, preferably 0.30 to 0.80; $b/(a+b+c)=0.01$ to 0.69, preferably 0.05 to 0.65; and $c/(a+b+c)=0.01$ to 0.20, preferably 0.05 to 0.10.

As another representation, a ratio "a:b:c" satisfies 100:1 to 230:1 to 67. a, b, and c represent ratios, n represents from 3 to 17, and X represents —H or a —OH group.

The combination of the phosphorylcholine constitutional unit, hydrophobic constitutional unit, and photoreactive constitutional unit of the copolymer of the present invention is as described below, but is not particularly limited (the left portion represents the phosphorylcholine constitutional unit, the central portion represents the hydrophobic constitutional unit, and the right portion represents the photoreactive constitutional unit).

MPC-butyl methacrylate-MBP
MPC-butyl methacrylate-MHP
MPC-hexyl methacrylate-MBP
MPC-hexyl methacrylate-MHP
MPC-2-ethylhexyl methacrylate-MBP
MPC-2-ethylhexyl methacrylate-MHP
MPC-decyl methacrylate-MBP
MPC-decyl methacrylate-MHP
MPC-dodecyl methacrylate-MBP
MPC-dodecyl methacrylate-MHP
MPC-tridecyl methacrylate-MBP
MPC-tridecyl methacrylate-MHP
MPC-stearyl methacrylate-MBP
MPC-stearyl methacrylate-MHP The ratio a of the phosphorylcholine constitutional unit of the copolymer of the present invention, the ratio b of the hydrophobic constitutional unit thereof, and the ratio c of the photoreactive constitutional unit thereof satisfy the following: $a/(a+b+c)=0.30$ to 0.90, preferably 0.30 to 0.80; $b/(a+b+c)=0.01$ to 0.69, preferably 0.05 to 0.65; and $c/(a+b+c)=0.01$ to 0.20, preferably 0.05 to 0.10.

As another representation, the ratio a of the phosphorylcholine constitutional unit of the copolymer of the present invention, the ratio b of the hydrophobic constitutional unit thereof, and the ratio c of the photoreactive constitutional unit thereof satisfy a ratio "a:b:c" of 100:1 to 230:1 to 67.

Further, as can be seen from Examples below, a more preferred combination of the phosphorylcholine constitutional unit, hydrophobic constitutional unit, and photoreactive constitutional unit of the copolymer of the present invention is MPC-butyl methacrylate-MBP (Synthesis Example 2). In addition, the ratio a of the phosphorylcholine constitutional unit of the copolymer of the present invention, the ratio b of the hydrophobic constitutional unit thereof, and the ratio c of the photoreactive constitutional unit thereof more preferably satisfy a ratio "a:b:c" of 0.5 to 0.7:0.2 to 0.4:0.05 to 0.15.

Next, an example of a method of producing the polymer of the present invention is described.

The copolymer of the present invention may be obtained by polymerizing, for example, a monomer composition containing 2-methacryloyloxyethyl-2-trimethylammonioethyl phosphate (MPC) represented by the following formula (3a), BMA represented by the following formula (3b: n=3), and MBP (X represents H) or MHP (X represents a OH group) represented by the following formula (3c), the monomer composition containing MPC at a molar ratio of from 0.30 to 0.90 with respect to the total amount of MPC, BMA, and MBP or MHP, BMA at a molar ratio of from 0.01 to 0.69 with respect thereto, and MBP or MHP at a molar ratio of from 0.01 to 0.20 with respect thereto.

The copolymer may further contain any other copolymerizable monomer as a constituent component.

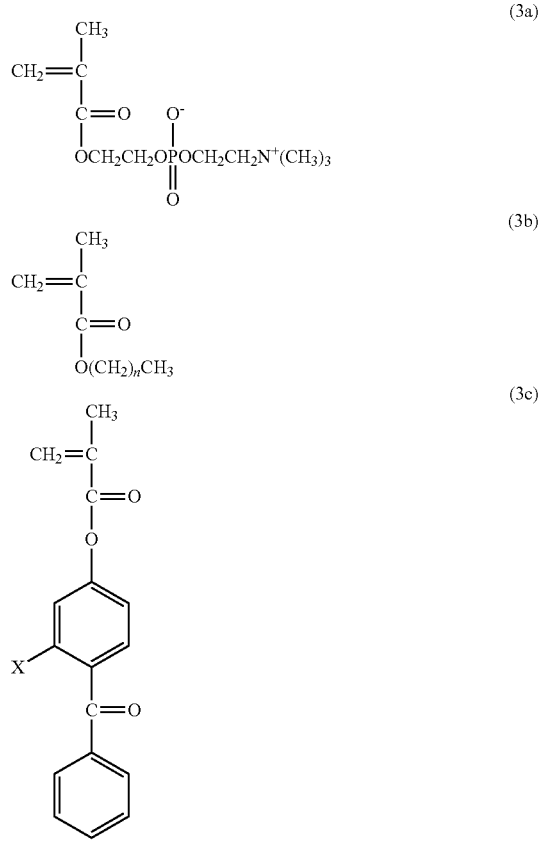

The polymerization reaction of the monomer composition may be performed by a known method, such as radical polymerization, such as bulk polymerization, suspension polymerization, emulsion polymerization, or solution polymerization, in the presence of, for example, a radical polymerization initiator after the inside of a reaction system has been replaced with an inert gas, such as nitrogen, carbon dioxide, argon, or helium, or in the inert gas atmosphere.

Of those, the solution polymerization is preferred from the viewpoint of, for example, the purification of the polymer to be obtained. The polymerization reaction provides a copolymer having the constitutional units represented by the formula (1a), the formula (1b), and the formula (1c). As described above, the copolymer may be a random copolymer, may be a block copolymer, or may be a copolymer in which a random moiety and a block moiety are mixed. In addition, an alternating copolymer moiety may be present.

When the copolymer is purified, the purification may be performed by a general purification method, such as a reprecipitation method, a dialysis method, or an ultrafiltration method.

Examples of the radical polymerization initiator include an azo-based radical polymerization initiator, an organic peroxide, and a persulfate.

Examples of the azo-based radical polymerization initiator include 2,2-azobis(2-aminopropyl) dihydrochloride, 2,2-azobis(2-(5-methyl-2-imidazolin-2-yl)propane) dihydrochloride, 4,4-azobis(4-cyanovaleric acid), 2,2-azobisisobutylamide dihydrate, 2,2-azobis(2,4-dimethylvaleronitrile), 2,2-azobisisobutyronitrile (AIBN), dimethyl-2,2'-azobisisobutyrate, 1-((1-cyano-1-methylethyl)azo)formamide, 2,2'-azobis(2-methyl-N-phenylpropionamidine) dihydrochloride, 2,2'-azobis(2-methyl-N-(2-hydroxyethyl)-propionamide), 2,2'-azobis(2-methylpropionamide) dihydrate, 4,4'-azobis(4-cyanopentanoic acid), and 2,2'-azobis(2-(hydroxymethyl) propionitrile).

Examples of the organic peroxide include benzoyl peroxide, diisopropyl peroxydicarbonate, t-butyl peroxy-2-ethylhexanoate, t-butyl peroxypivalate, t-butyl peroxydiisobutyrate, lauroyl peroxide, t-butyl peroxyneodecanoate, succinic acid peroxide (=succinylperoxide), glutaricperoxide, succinylperoxyglutarate, t-butyl peroxymalate, t-butyl peroxypivalate, di-2-ethoxyethyl peroxycarbonate, and 3-hydroxy-1,1-dimethylbutyl peroxypivalate.

Examples of the persulfate include ammonium persulfate, potassium persulfate, and sodium persulfate.

Those radical polymerization initiators may be used alone or as a mixture thereof. The usage amount of the polymerization initiator is typically from 0.001 part by mass to 10 parts by mass, preferably from 0.01 part by mass to 5.0 parts by mass with respect to 100 parts by mass of the monomer composition.

The polymerization reaction of the monomer composition may be performed in the presence of a solvent. A solvent that dissolves the monomer composition and does not react with the monomer composition before the addition of the polymerization initiator may be used as the solvent. For example, there are given water, an alcohol-based solvent, a ketone-based solvent, an ester-based solvent, an ether-based solvent, and a nitrogen-containing solvent. Examples of the alcohol-based solvent include methanol, ethanol, n-propanol, and isopropanol. Examples of the ketone-based solvent include acetone, methyl ethyl ketone, and diethyl ketone. An example of the ester-based solvent is ethyl acetate. Examples of the ether-based solvent include ethyl cellosolve, tetrahydrofuran, and N-methylpyrrolidone. Examples of the nitrogen-containing solvent include acetonitrile and nitromethane. There are preferably given water, alcohol, and a mixed solvent thereof.

Although a proper temperature only needs to be selected as a temperature at the time of the polymerization reaction as appropriate in accordance with the kinds of the polymerization initiator and the solvent to be used, and a desired molecular weight, the temperature preferably falls within the range of from 40° C. to 100° C.

Next, a method of forming a crosslinked body from the polymer of the present invention on the surface of a substrate to be made biocompatible is described.

When the crosslinked body is formed from the polymer of the present invention on the substrate, the following only needs to be adopted: the polymer of the present invention is dissolved in a proper solvent that can dissolve the polymer, such as water, physiological saline, various buffers (e.g., a phosphate buffer and a carbonate buffer), ethanol, methanol, propanol, or isopropanol, or a mixture thereof, and the polymer of the present invention is applied onto the target substrate. The polymer is more preferably caused to exist in the solution at 0.02 mg/cm² or more.

In order to form the crosslinked body on the substrate surface, the substrate having applied thereto the polymer only needs to be irradiated with UV light having a wavelength of from 200 nm to 360 nm. The substrate is more preferably irradiated with light having a wavelength of about 254 nm.

The surface treatment agent of the present invention contains 0.01 wt % to 5 wt %, preferably 0.1 wt % to 2.5 wt %, more preferably 0.1 wt % to 1.0 wt % of the polymer of the present invention.

The substrate to be used in this case is preferably a substrate that can abstract a proton, and examples thereof include various plastic materials, such as polystyrene, polypropylene, polymethyl methacrylate, polyethylene, cyclic polyolefin, polydimethylsiloxane, polyester, and polyurethane. Further, the shape of any such substrate has a shape in accordance with its use purpose. For example, the substrate has a shape such as a plate shape, a petri dish shape, a shape having many holes, or a shape having formed therein a precise channel.

The crosslinked body formed from the polymer of the present invention has a three-dimensional network structure in which polymer chains are crosslinked, is excellent in biocompatibility, hydrophilicity, hydrous property, structural flexibility, substance absorbability, and the like, and is excellent particularly in biocompatibility. Therefore, the formation of the crosslinked body, which is formed from the polymer of the present invention, on the substrate surface can impart biocompatibility to the substrate. In general, the biocompatibility of a phosphorylcholine group is blood compatibility, which has a feature in that a protein or a cell does not adsorb or adhere to the substrate surface.

In addition, the utilization of those properties enables the development of the crosslinked body into medical devices, such as: a drug sustained-release carrier; a cell scaffold; a surface-modifying material; and a wound healing accelerator, such as a hemostatic.

Specific examples of the medical device of the present invention may include: a contact lens; a substrate functioning as a scaffold for a transplanted cell; a wound dressing agent; a wound healing accelerator; a hemostatic; a drug sustained-release material; a surface-modifying material; a substrate for a diagnostic agent to be used in immunochromatography, ELISA, or the like; a substrate for cell culture, such as a petri dish, a microplate, a flask, or a bag; a microchannel; and a cell.

An application for producing the surface treatment agent of the present invention is also a subject matter of the present invention.

An application for producing a surface treatment agent using a copolymer including constitutional units represented by the following formula (1a) to the following formula (1c), in which: ratios a, b, and c of the respective constitutional units satisfy the following: a/(a+b+c)=0.30 to 0.90; b/(a+b+c)=0.01 to 0.69; and c/(a+b+c)=0.01 to 0.20; and the copolymer has a weight-average molecular weight of from 10,000 to 1,000,000:

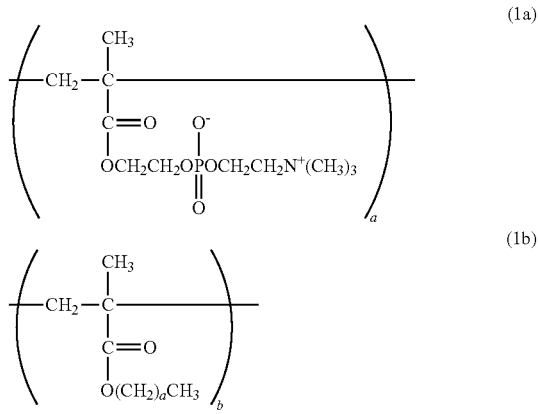

where n represents from 3 to 17;

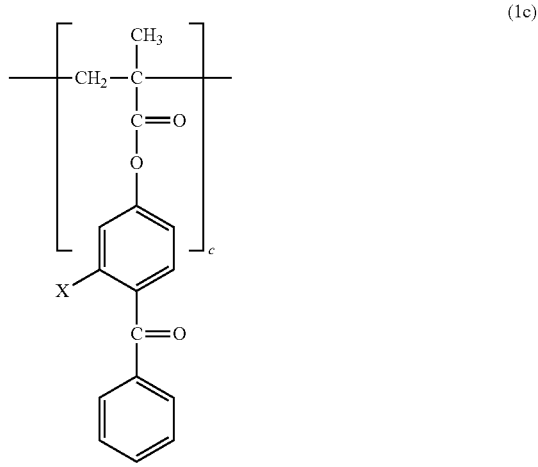

where X represents —H or a —OH group.

EXAMPLES

Now, the present invention is described in more detail byway of Examples. However, the present invention is not limited thereto. Various measurements in Synthesis Examples were performed in accordance with the following methods.

<Measurement of Weight-Average Molecular Weight>

5 mg of the resultant polymer is dissolved in 1 g of a 0.1 mol/L aqueous solution of sodium sulfate, and its weight-average molecular weight is measured by gel permeation chromatography (GPC). Measurement conditions are as described below.

Apparatus: RI-8020, DP-8020, SD-8022, and AS-8020 (manufactured by Tosoh Corporation), and 865-CO (manufactured by JASCO Corporation), column: Shodex OHpak (manufactured by Showa Denko K.K.), mobile phase: a 0.1 mol/L aqueous solution of sodium sulfate, standard substance: pullulan, detection: a differential refractometer, calculation of weight-average molecular weight (Mw): a molecular weight calculation program (GPC program for SC-8020), flow rate: 1.0 ml/min, column temperature: 40° C., sample solution injection amount: 100 μL, measurement time: 30 minutes.

Synthesis Example 1

18.2335 g (0.0618 mol) of 2-methacryloyloxyethyl-2-trimethylammonioethyl phosphate (MPC), 19.0257 g (0.134 mol) of butyl methacrylate (BMA), and 2.7408 g (0.0103 mol) of 4-methacryloyloxybenzophenone (MBP) were dissolved in 155.1124 g of ethanol (EtOH). The solution was loaded into a 300-milliliter four-necked flask with a temperature gauge and a condenser, and nitrogen was blown into the flask for 30 minutes. After that, 4.8876 g (2.98 mmol) of a 10 wt % solution of azobisisobutyronitrile (AIBN) in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 1

($^1$H NMR)
0.70-1.35 ppm (—C$\underline{H}_3$), 1.35-2.60 ppm (—C$\underline{H}_2$—C—, —O—CH$_2$—C$\underline{H}_2$—C$\underline{H}_2$—CH$_3$), 3.15-3.40 ppm (—N$^+$(C$\underline{H}_3$)$_3$), 3.60-3.80 ppm (—C$\underline{H}_2$—N$^+$(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—CH$_2$—O—P—), 7.20-8.00 ppm (—C$_6\underline{H}_4$—C(O)—C$_6\underline{H}_5$)

It was confirmed from the foregoing results that the polymer had a ratio based on MPC represented by the formula (2a) of 30 mol %, a ratio based on BMA represented by the formula (2b) (n=3) of 65 mol %, a ratio based on MBP represented by the formula (2c) of 5 mol %, and a weight-average molecular weight of 18,000.

Synthesis Example 2

28.7540 g (0.0974 mol) of MPC, 6.9239 g (0.0487 mol) of BMA, and 4.3221 g (0.0162 mol) of MBP were dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 2

($^1$H NMR)
0.70-1.35 ppm (—C$\underline{H}_3$), 1.35-2.60 ppm (—C$\underline{H}_2$—C—, —O—CH$_2$—C$\underline{H}_2$—C$\underline{H}_2$—CH$_3$), 3.15-3.40 ppm (—N$^+$(C$\underline{H}_3$)$_3$), 3.60-3.80 ppm (—C$\underline{H}_2$—N$^+$(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—CH$_2$—O—P—), 7.20-8.00 ppm (—C$_6\underline{H}_4$—C(O)—C$_6\underline{H}_5$)

It was confirmed from the foregoing results that the polymer had a ratio based on MPC represented by the formula (2a) of 60 mol %, a ratio based on BMA represented by the formula (2b) (n=3) of 30 mol %, a ratio based on MBP represented by the formula (2c) of 10 mol %, and a weight-average molecular weight of 118,000.

Synthesis Example 3

35.5350 g (0.120 mol) of MPC, 4.0644 g (0.0286 mol) of BMA, and 0.4006 g (0.00150 mol) of MBP were dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 3

($^1$H NMR)
0.70-1.35 ppm (—C$\underline{H}_3$), 1.35-2.60 ppm (—C$\underline{H}_2$—C—, —O—CH$_2$—C$\underline{H}_2$—C$\underline{H}_2$—CH$_3$), 3.15-3.40 ppm (—N$^+$(C$\underline{H}_3$)$_3$), 3.60-3.80 ppm (—C$\underline{H}_2$—N+(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—CH$_2$—O—P—), 7.20-8.00 ppm (—C$_6\underline{H}_4$—C(O)—C$_6\underline{H}_5$)

It was confirmed from the foregoing results that the polymer had a ratio based on MPC represented by the formula (2a) of 80 mol %, a ratio based on BMA represented by the formula (2b) (n=3) of 19 mol %, a ratio based on MBP represented by the formula (2c) of 1 mol %, and a weight-average molecular weight of 145,000.

Synthesis Example 4

34.1025 g (0.116 mol) of MPC, 2.0529 g (0.0144 mol) of BMA, and 3.8446 g (0.0144 mol) of MBP were dissolved in 115.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 60° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 4

($^1$H NMR)
0.70-1.35 ppm (—C$\underline{H}_3$), 1.35-2.60 ppm (—C$\underline{H}_2$—C—, —O—CH$_2$—C$\underline{H}_2$—C$\underline{H}_2$—CH$_3$), 3.15-3.40 ppm (—N$^+$(C$\underline{H}_3$)$_3$), 3.60-3.80 ppm (—C$\underline{H}_2$—N$^+$(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—C$\underline{H}_2$—O—P—), 7.20-8.00 ppm (—C$_6$$\underline{H}_4$—C(O)—C$_6$$\underline{H}_5$)

It was confirmed from the foregoing results that the polymer had a ratio based on MPC represented by the formula (2a) of 80 mol %, a ratio based on BMA represented by the formula (2b) (n=3) of 10 mol %, a ratio based on MBP represented by the formula (2c) of 10 mol %, and a weight-average molecular weight of 520,000.

Synthesis Example 5

32.7810 g (0.111 mol) of MPC, 0.1973 g (0.00139 mol) of BMA, and 7.0217 g (0.0264 mol) of MBP were dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 5

($^1$H NMR)
0.70-1.35 ppm (—C$\underline{H}_3$), 1.35-2.60 ppm (—C$\underline{H}_2$—C—, —O—CH$_2$—C$\underline{H}_2$—C$\underline{H}_2$—CH$_3$), 3.15-3.40 ppm (—N$^+$(C$\underline{H}_3$)$_3$), 3.60-3.80 ppm (—C$\underline{H}_2$—N$^+$(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—C$\underline{H}_2$—O—P—), 7.20-8.00 ppm (—C$_6$$\underline{H}_4$—C(O)—C$_6$$\underline{H}_5$)

It was confirmed from the foregoing results that the polymer had a ratio based on MPC represented by the formula (2a) of 80 mol %, a ratio based on BMA represented by the formula (2b) (n=3) of 1 mol %, a ratio based on MBP represented by the formula (2c) of 19 mol %, and a weight-average molecular weight of 135,000.

Synthesis Example 6

28.5686 g (0.0968 mol) of MPC, 6.8793 g (0.0484 mol) of BMA, and 4.5521 g (0.0161 mol) of MHP were dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 6

($^1$H NMR)
0.70-1.35 ppm (—C$\underline{H}_3$), 1.35-2.60 ppm (—C$\underline{H}_2$—C—, —O—CH$_2$—C$\underline{H}_2$—C$\underline{H}_2$—CH$_3$), 3.15-3.40 ppm (—N$^+$(C$\underline{H}_3$)$_3$), 3.60-3.80 ppm (—C$\underline{H}_2$—N$^+$(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—C$\underline{H}_2$—O—P—), 7.20-8.00 ppm (—C$_6$$\underline{H}_3$(OH)—C(O)—C$_6$$\underline{H}_5$)

It was confirmed from the foregoing results that the polymer had a ratio based on MPC represented by the formula (2a) of 60 mol %, a ratio based on BMA represented by the formula (2b) (n=3) of 30 mol %, a ratio based on MHP represented by the formula (2c) of 10 mol %, and a weight-average molecular weight of 120,000.

Synthesis Example 7

31.8408 g (0.108 mol) of MPC, 4.5696 g (0.0135 mol) of stearyl methacrylate (SMA), and 3.5896 g (0.0135 mol) of MBP were dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Synthesis Example 7

($^1$H NMR)
0.70-1.35 ppm (—C$\underline{H}_3$), 1.35-2.60 ppm (—C$\underline{H}_2$—C—, —O—CH$_2$—(C$\underline{H}_2$)$_{16}$—CH$_3$), 3.15-3.40 ppm (—N$^+$(C$\underline{H}_3$)$_3$), 3.60-3.80 ppm (—C$\underline{H}_2$—N$^+$(CH$_3$)$_3$), 3.80-4.15 ppm (—P—O—C$\underline{H}_2$—, —C(O)—O—C$\underline{H}_2$—CH$_2$—), 4.15-4.40 ppm (—O—C$\underline{H}_2$—C$\underline{H}_2$—O—P—), 7.20-8.00 ppm (—C$_6$$\underline{H}_4$—C(O)—C$_6$$\underline{H}_5$)

It was confirmed from the foregoing results that the polymer had a ratio based on MPC represented by the formula (2a) of 80 mol %, a ratio based on SMA represented by the formula (2b) (n=17) of 10 mol %, a ratio based on MBP represented by the formula (2c) of 10 mol %, and a weight-average molecular weight of 120,000.

Comparative Synthesis Example 1

40.0000 g (0.136 mol) of MPC was dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The resultant polymer was subjected to the respective measurements in the same manner as in Synthesis Example 1. The measurement results of its $^1$H NMR and weight-average molecular weight are shown below and in Table 1.

Polymer of Comparative Synthesis Example 1

($^1$H NMR)
0.70-1.45 ppm (—C$\underline{H_3}$), 1.45-2.60 ppm (—C$\underline{H_2}$—C—), 3.20-3.40 ppm (—N$^+$(C$\underline{H_3}$)$_3$), 3.60-3.80 ppm (—C$\underline{H_2}$—N$^+$(CH$_3$)$_3$), 4.00-4.15 ppm (—P—O—C$\underline{H_2}$—), 4.15-4.40 ppm (—O—C$\underline{H_2}$—C$\underline{H_2}$—O—P—)

It was confirmed from the foregoing results that the polymer had a ratio based on MPC represented by the formula (2a) of 100 mol % and a weight-average molecular weight of 188,000.

Comparative Synthesis Example 2

35.9400 g (0.122 mol) of MPC and 4.0600 g (0.0286 mol) of BMA were dissolved in 155.1124 g of EtOH. The solution was loaded into a 300-milliliter four-necked flask with a temperature gauge and a condenser, and nitrogen was blown into the flask for 30 minutes. After that, 4.8876 g (2.98 mmol) of a 10 wt % solution of AIBN in EtOH was added to the solution at 65° C., and a polymerization reaction was performed for 6 hours. Thus, a polymer formed of the monomer feed composition was obtained. After the completion of the reaction, the polymer was purified by precipitation in diethyl ether. The measurement results of the $^1$H NMR and weight-average molecular weight of the resultant polymer are shown below and in Table 1.

Polymer of Comparative Synthesis Example 2

($^1$H NMR)
0.70-1.35 ppm (—C$\underline{H_3}$), 1.35-2.60 ppm (—C$\underline{H_2}$—C—, —O—CH$_2$—C$\underline{H_2}$—C$\underline{H_2}$—CH$_3$), 3.15-3.40 ppm (—N$^+$(C$\underline{H_3}$)$_3$), 3.60-3.80 ppm (—C$\underline{H_2}$—N$^+$(CH$_3$)$_3$), 3.80-4.15 ppm (—P—O—C$\underline{H_2}$—, —C(O)—O—C$\underline{H_2}$—CH$_2$—), 4.15-4.40 ppm (—O—C$\underline{H_2}$—CH$_2$—O—P—)

It was confirmed from the foregoing results that the polymer had a ratio based on MPC represented by the formula (2a) of 81 mol %, a ratio based on BMA represented by the formula (2b) of 19 mol %, and a weight-average molecular weight of 138,000.

Comparative Synthesis Example 3

18.2000 g (0.0616 mol) of MPC and 1.2000 g (7.25 mmol) of aminoethyl methacrylate (AEMA) free of any benzophenone group were dissolved in 80.0 g of ion-exchanged water. The solution was loaded into a 300-milliliter four-necked flask with a temperature gauge and a condenser, and nitrogen was blown into the flask for 30 minutes. After that, 0.1492 g (0.550 mmol) of 2,2'-azobis (2-methylpropionamidine) dihydrochloride (V-50) was added to the solution at 60° C., and a polymerization reaction was performed for 8 hours. Thus, a polymer formed of the monomer feed composition was obtained. After the completion of the reaction, the polymer was purified by dialysis. The chemical structure of the resultant polymer was identified by $^1$H NMR. In addition, the measurement result of its weight-average molecular weight is shown below and in Table 1.

Polymer of Comparative Synthesis Example 3

($^1$H NMR)
0.70-1.45 ppm (—C$\underline{H_3}$), 1.45-2.60 ppm (—C$\underline{H_2}$—C—), 3.20-3.40 ppm (—N$^+$(C$\underline{H_3}$)$_3$), 3.20-3.50 ppm (—C$\underline{H_2}$—NH$_2$), 3.60-3.80 ppm (—C$\underline{H_2}$—N$^+$(CH$_3$)$_3$), 4.00-4.15 ppm (—P—O—C$\underline{H_2}$—), 4.15-4.40 ppm (—C(O)—O—C$\underline{H_2}$—, —O—C$\underline{H_2}$—CH$_2$—O—P—)

It was confirmed from the foregoing results that the polymer had a ratio based on MPC represented by the formula (2a) of 90 mol %, a ratio based on AEMA of 10 mol %, and a weight-average molecular weight of 800,000.

TABLE 1

| | | Synthesis Example | | | | | | | Comparative Synthesis Example | | |
|---|---|---|---|---|---|---|---|---|---|---|---|
| | | 1 | 2 | 3 | 4 | 5 | 6 | 7 | 1 | 2 | 3 |
| Monomer (g) | MPC | 18.2335 | 28.754 | 35.535 | 34.1025 | 32.781 | 28.5686 | 31.8408 | 40 | 35.94 | 18.2 |
| | BMA | 19.0257 | 6.9239 | 4.0644 | 2.0529 | 0.1973 | 6.8793 | — | — | 4.06 | — |
| | SMA | — | — | — | — | — | — | 4.5696 | — | — | — |
| | MBP | 2.7408 | 4.3221 | 0.4006 | 3.8446 | 7.0217 | — | 3.5896 | — | — | — |
| | MHP | — | — | — | — | — | 4.5521 | — | — | — | — |
| | AEMA | — | — | — | — | — | — | — | — | — | 1.2 |
| Solvent (g) | EtOH or ion-exchanged water | 155.1124 | 155.1124 | 155.1124 | 155.1124 | 155.1124 | 155.1124 | 155.1124 | 155.1124 | 155.1124 | 80.0 |
| Initiator (g) | AIBN sol. or V50 | 4.8876 | 4.8876 | 4.8876 | 4.8876 | 4.8876 | 4.8876 | 4.8876 | 4.8876 | 4.8876 | 0.1492 |
| Water solubility | | ○ | ○ | ○ | ○ | ○ | ○ | ○ | ○ | ○ | ○ |
| Feed composition ratio (MPC/BMA or SMA/MBP or MHP or AEMA) | | 0.30/0.65/0.05 | 0.60/0.30/0.10 | 0.80/0.19/0.01 | 0.80/0.10/0.10 | 0.80/0.01/0.19 | 0.60/0.30/0.10 | 0.80/0.10/0.10 | 1.00/0/0 | 0.81/0.19/0 | 0.90/0/0.10 |
| Polymer composition ratio (MPC/BMA or SMA/MBP or MHP or AEMA) | | 0.30/0.65/0.05 | 0.60/0.30/0.10 | 0.80/0.19/0.01 | 0.80/0.10/0.10 | 0.80/0.01/0.19 | 0.60/0.30/0.10 | 0.80/0.10/0.10 | 1.00/0/0 | 0.81/0.19/0 | 0.90/0/0.10 |
| Molecular weight (×10$^3$) | | 18 | 118 | 145 | 520 | 135 | 120 | 120 | 188 | 138 | 800 |

Example 1-1-1

The polymer of Synthesis Example 1 was dissolved in ethanol so that its concentration became 0.5 wt %, and a polymer coating was formed on each well bottom surface of a 96-well plate made of polystyrene (manufactured by Watson Biolab) so that its amount became 0.02 mg/cm$^2$. After that, the plate was irradiated with light having a wavelength of 254 nm for 7 minutes by using DNA-FIX (manufactured by ATTO Corporation). After the photoirradiation, ethanol was added in an amount of 200 μL/well, and the plate was left at rest at room temperature for 2 hours. After that, ethanol was removed, and fresh ethanol was added in an amount of 200 μL/well and removed; the washing step was performed three times. After the washing with ethanol, HRP-labeled IgG (manufactured by Bio-Rad Laboratories, Inc.) diluted 24,000-fold with DULBECCOS'S PHOSPHATE BUFFERED SALINE (hereinafter referred to as "PBS") was added in an amount of 100 μL/well, and the plate was left at rest at room temperature for 1 hour. The HRP-labeled IgG solution in each well was removed, and a phosphate buffer containing 0.05% Tween 20 was added in an amount of 200 μL/well and removed; the washing step was repeated four times. After the washing, a chromogenic liquid for HRP (manufactured by KPL) was added in an amount of 100 μL/well, and a reaction was performed at room temperature for 10 minutes. After a lapse of 10 minutes, 2 N sulfuric acid was added in an amount of 50 μL/well to terminate the reaction, and an absorbance at 450 nm was measured. Thus, the protein adsorbing to the inside of each well was detected.

Example 1-1-2

A sample was prepared by using the polymer of Synthesis Example 1 so that a polymer amount in each well became 0.08 mg/cm$^2$, followed by the performance of the same experiment as that of Example 1-1-1.

Example 1-1-3

A sample was prepared by using the polymer of Synthesis Example 1 so that a polymer amount in each well became 0.12 mg/cm$^2$, followed by the performance of the same experiment as that of Example 1-1-1.

Examples 1-2-1 to 1-7-3

Samples were prepared by using the polymers of Synthesis Examples 2 to 7 so that a polymer amount in each well became 0.02 mg/cm$^2$, 0.08 mg/cm$^2$, or 0.12 mg/cm$^2$, followed by the performance of the same experiment as that of Example 1-1-1.

Comparative Examples 1-1-1 to 1-3-3

Samples were prepared by using the polymers of Comparative Synthesis Example 1, Comparative Synthesis Example 2, and Comparative Synthesis Example 3 so that a polymer amount in each well became 0.02 mg/cm$^2$, 0.08 mg/cm$^2$, or 0.12 mg/cm$^2$, followed by the performance of the same experiment as that of Example 1-1-1.

Comparative Example 1-4

The same experiment as that of Comparative Example 1-1-1 was performed by using a 96-well plate made of polystyrene (manufactured by Watson Biolab) free of any polymer coating.

The absorbance of a well free of any polymer coating was defined as a protein adsorption ratio of 100%, and the protein adsorption ratios of Examples 1-1-1 to 1-7-3 and Comparative Examples 1-1-1 to 1-3-3 were calculated.

The absorbances and the protein adsorption ratios thus obtained were shown in Table 2.

As is apparent from Table 2, it was confirmed that when the crosslinked body of each of the polymers of Synthesis Examples 1 to 7 was formed on the substrate surface and the resultant was irradiated with light, the substrate surface suppressing the adsorption of the protein (HRP-labeled IgG) was able to be formed.

Meanwhile, in each of Comparative Synthesis Example 1 (polymer free of any hydrophobic constitutional unit and any photoreactive constitutional unit), Comparative Synthesis Example 2 (polymer free of any photoreactive constitutional unit), and Comparative Synthesis Example 3 (polymer free of any hydrophobic constitutional unit and any benzophenone group, but having an amino group), the following result was obtained: no polymer crosslinked body was formed on the substrate surface by the photoirradiation, and hence the protein adhered to the substrate surface.

It was confirmed from the foregoing results that the crosslinked body of the present invention was able to impart such biocompatibility that the adsorption of the protein was prevented through the irradiation of a substrate surface with light.

TABLE 2

Protein adsorption test

| Test No. | Kind of polymer | Polymer amount (mg/cm$^2$) | Absorbance (450 nm) | Protein adsorption ratio (%) |
| --- | --- | --- | --- | --- |
| Example 1-1-1 | Synthesis Example 1 | 0.02 | 0.254 | 19.4 |
| Example 1-1-2 | | 0.08 | 0.212 | 16.2 |
| Example 1-1-3 | | 0.12 | 0.248 | 18.9 |
| Example 1-2-1 | Synthesis Example 2 | 0.02 | 0.114 | 8.7 |
| Example 1-2-2 | | 0.08 | 0.118 | 9.0 |
| Example 1-2-3 | | 0.12 | 0.107 | 8.2 |
| Example 1-3-1 | Synthesis Example 3 | 0.02 | 0.205 | 15.6 |
| Example 1-3-2 | | 0.08 | 0.175 | 13.4 |
| Example 1-3-3 | | 0.12 | 0.153 | 11.7 |
| Example 1-4-1 | Synthesis Example 4 | 0.02 | 0.211 | 16.1 |
| Example 1-4-2 | | 0.08 | 0.198 | 15.1 |
| Example 1-4-3 | | 0.12 | 0.187 | 14.3 |
| Example 1-5-1 | Synthesis Example 5 | 0.02 | 0.297 | 22.7 |
| Example 1-5-2 | | 0.08 | 0.248 | 18.9 |
| Example 1-5-3 | | 0.12 | 0.241 | 18.4 |
| Example 1-6-1 | Synthesis Example 6 | 0.02 | 0.182 | 13.9 |
| Example 1-6-2 | | 0.08 | 0.168 | 12.8 |
| Example 1-6-3 | | 0.12 | 0.175 | 13.4 |
| Example 1-7-1 | Synthesis Example 7 | 0.02 | 0.201 | 15.3 |
| Example 1-7-2 | | 0.08 | 0.172 | 13.1 |
| Example 1-7-3 | | 0.12 | 0.151 | 11.5 |
| Comparative Example 1-1-1 | Comparative Synthesis Example 1 | 0.02 | 1.25 | 95.4 |
| Comparative Example 1-1-2 | | 0.08 | 1.319 | 100.7 |
| Comparative Example 1-1-3 | | 0.12 | 1.32 | 100.8 |
| Comparative Example 1-2-1 | Comparative Synthesis Example 2 | 0.02 | 1.326 | 101.2 |
| Comparative Example 1-2-2 | | 0.08 | 1.364 | 104.1 |
| Comparative Example 1-2-3 | | 0.12 | 1.235 | 94.3 |
| Comparative Example 1-3-1 | Comparative Synthesis Example 3 | 0.02 | 1.365 | 104.2 |
| Comparative Example 1-3-2 | | 0.08 | 1.314 | 100.3 |
| Comparative Example 1-3-3 | | 0.12 | 1.287 | 98.2 |
| Comparative Example 1-4 | — | — | 1.31 | 100.0 |

Example 2-1-1

The polymer of Synthesis Example 1 was dissolved in ethanol so that its concentration became 0.5 wt %, and a polymer coating was formed on each well bottom surface of a 96-well plate made of polystyrene (manufactured by Watson Biolab) so that its amount became 0.02 mg/cm$^2$.

After that, the plate was irradiated with light having a wavelength of 254 nm for 7 minutes by using DNA-FIX (manufactured by ATTO Corporation). After the photoirradiation, ethanol was added in an amount of 200 μL/well, and the plate was left at rest at room temperature for 2 hours. After that, ethanol was removed, and fresh ethanol was added in an amount of 200 μL/well and removed; the washing step was performed three times. The plate was dried for 3 hours while being irradiated with light from a UV lamp in a clean bench. Mouse embryonic carcinoma cells P19.CL6 cells (hereinafter referred to as "P19") cultured by using a MEMα medium (manufactured by Invitrogen, hereinafter referred to as "P19 medium") containing 10% fetal bovine serum (manufactured by GIBCO) and 1% penicillin-streptomycin (manufactured by Sigma-Aldrich) were recovered by a 0.25% trypsin treatment, and were diluted with the P19 medium so as to have a concentration of 5,000 cells/mL. The diluted cells were inoculated in an amount of 100 μL/well, and were cultured in a 5% $CO_2$ incubator (hereinafter referred to as "incubator") at 37° C. for 3 days. After a lapse of 3 days, the medium was removed and a P19 medium containing 0.5 mg/mL of MTT was added in an amount of 100 μL/well, followed by culture in the incubator for 1 hour. After a lapse of 1 hour, the medium was removed and the PBS was gently added in an amount of 100 μL/well, followed by the removal of the PBS. After that, dimethylsulfoxide (manufactured by Kishida Chemical Co., Ltd.) was added in an amount of 100 μL/well. While the plate was shaken at room temperature for 10 minutes, a dye was extracted and its absorbance at 570 nm was measured with a microplate reader (SPECTRA Max M3, manufactured by Molecular Devices).

Example 2-1-2

A sample was prepared by using the polymer of Synthesis Example 1 so that a polymer amount in each well became 0.08 mg/cm², followed by the performance of the same experiment as that of Example 2-1-1.

Example 2-1-3

A sample was prepared by using the polymer of Synthesis Example 1 so that a polymer amount in each well became 0.12 mg/cm², followed by the performance of the same experiment as that of Example 2-1-1.

Examples 2-2-1 to 2-5-3

Samples were prepared by using the polymers of Synthesis Examples 1, 2, 3, 6, and 7 so that a polymer amount in each well became 0.02 mg/cm², 0.08 mg/cm², or 0.12 mg/cm², followed by the performance of the same experiment as that of Example 2-1-1.

Comparative Examples 2-1-1 to 2-3-3

Samples were prepared by using the polymers of Comparative Synthesis Example 1, Comparative Synthesis Example 2, and Comparative Synthesis Example 3 so that a polymer amount in each well became 0.02 mg/cm², 0.08 mg/cm², or 0.12 mg/cm², followed by the performance of the same experiment as that of Example 2-1-1.

Comparative Example 2-4

The same experiment as that of Comparative Example 1-1-1 was performed by using a 96-well plate made of polystyrene (manufactured by Watson Biolab) free of any polymer coating.

The absorbance of a well free of any polymer coating (Comparative Example 2-4) was defined as a cell adhesion ratio of 100%, and the cell adhesion ratios of Examples 2-1-1 to 2-5-3 and Comparative Examples 2-1-1 to 2-3-3 were calculated.

The absorbances and the cell adhesion ratios thus obtained were shown in Table 3.

TABLE 3

| | Cell Adhesion Test | | | |
|---|---|---|---|---|
| Test No. | Kind of polymer | Polymer amount (mg/cm²) | Absorbance (570 nm) | Cell adhesion ratio (%) |
| Example 2-1-1 | Synthesis Example 1 | 0.02 | 0.154 | 20.0 |
| Example 2-1-2 | | 0.08 | 0.148 | 19.2 |
| Example 2-1-3 | | 0.12 | 0.115 | 14.9 |
| Example 2-2-1 | Synthesis Example 2 | 0.02 | 0.171 | 22.2 |
| Example 2-2-2 | | 0.08 | 0.121 | 15.7 |
| Example 2-2-3 | | 0.12 | 0.063 | 8.2 |
| Example 2-3-1 | Synthesis Example 3 | 0.02 | 0.184 | 23.9 |
| Example 2-3-2 | | 0.08 | 0.215 | 27.9 |
| Example 2-3-3 | | 0.12 | 0.157 | 20.4 |
| Example 2-4-1 | Synthesis Example 6 | 0.02 | 0.135 | 17.5 |
| Example 2-4-2 | | 0.08 | 0.162 | 21.0 |
| Example 2-4-3 | | 0.12 | 0.104 | 13.5 |
| Example 2-5-1 | Synthesis Example 7 | 0.02 | 0.173 | 22.5 |
| Example 2-5-2 | | 0.08 | 0.142 | 18.4 |
| Example 2-5-3 | | 0.12 | 0.107 | 13.9 |
| Comparative Example 2-1-1 | Comparative Synthesis Example 1 | 0.02 | 0.724 | 94.0 |
| Comparative Example 2-1-2 | | 0.08 | 0.794 | 103.1 |
| Comparative Example 2-1-3 | | 0.12 | 0.613 | 79.6 |
| Comparative Example 2-2-1 | Comparative Synthesis Example 2 | 0.02 | 0.826 | 107.3 |
| Comparative Example 2-2-2 | | 0.08 | 0.786 | 102.1 |
| Comparative Example 2-2-3 | | 0.12 | 0.735 | 95.5 |
| Comparative Example 2-3-1 | Comparative Synthesis Example 3 | 0.02 | 0.754 | 97.9 |
| Comparative Example 2-3-2 | | 0.08 | 0.781 | 101.4 |
| Comparative Example 2-3-3 | | 0.12 | 0.768 | 99.7 |
| Comparative Example 2-4 | — | — | 0.770 | 100.0 |

As is apparent from Table 3, it was confirmed that when the crosslinked body formed of each of the polymers of Synthesis Examples 1, 2, 3, 6, and 7 was formed on the substrate surface and the resultant was irradiated with light, the substrate surface suppressing the adhesion of the cells was able to be formed.

Meanwhile, in each of Comparative Synthesis Example 1 (polymer free of any hydrophobic constitutional unit and any photoreactive constitutional unit), Comparative Synthesis Example 2 (polymer free of any photoreactive constitutional unit), and Comparative Synthesis Example 3 (polymer free of any hydrophobic constitutional unit and any benzophenone group, but having an amino group), the following result was obtained: no polymer crosslinked body was formed on the substrate surface by the photoirradiation, and hence the cells adhered to the substrate surface.

It was confirmed from the foregoing results that the crosslinked body of the present invention was able to impart such biocompatibility that the adsorption of the cells was prevented through the irradiation of a substrate surface with light.

It was confirmed from the foregoing results that a protein, a cell, or the like did not adhere to the crosslinked body of the present invention. Accordingly, a medical device including the crosslinked body of the present invention has high biocompatibility.

INDUSTRIAL APPLICABILITY

There can be provided a novel copolymer and a crosslinked body formed from the copolymer.

The invention claimed is:

1. A copolymer, comprising constitutional units represented by the following formula (1a) to the following formula (1c), wherein:
   ratios a, b, and c of the respective constitutional units satisfy the following:

$a/(a+b+c)=0.30$ to $0.90$;

$b/(a+b+c)=0.01$ to $0.69$; and $c/(a+b+c)=0.01$ to $0.20$; and the copolymer has a weight-average molecular weight of from 10,000 to 1,000,000:

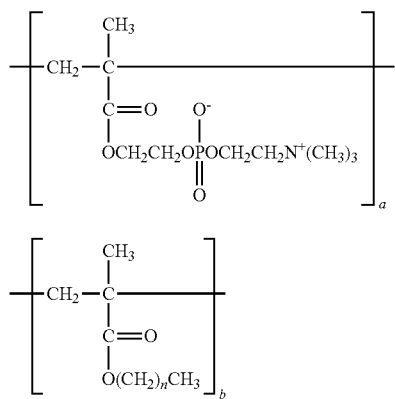

where n represents from 3 to 17;

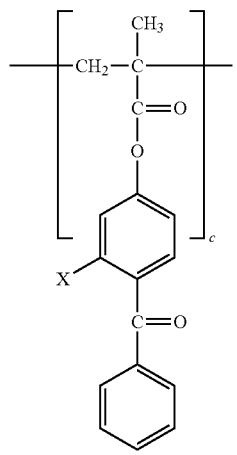

where X represents —H or a —OH group.

2. A copolymer according to claim 1, wherein the constitutional unit represented by the formula (1a) comprises 2-methacryloyloxyethyl-2-trimethylammonioethyl phosphate, the constitutional unit represented by the formula (1b) comprises butyl methacrylate, and the constitutional unit represented by the formula (1c) comprises 4-methacryloyloxybenzophenone.

3. A copolymer according to claim 1, wherein the constitutional unit represented by the formula (1a) comprises 2-methacryloyloxyethyl-2-trimethylammonioethyl phosphate, the constitutional unit represented by the formula (1b) comprises butyl methacrylate, and the constitutional unit represented by the formula (1c) comprises 4-methacryloyloxy-2-hydroxybenzophenone.

4. A copolymer according to claim 1, wherein the constitutional unit represented by the formula (1a) comprises 2-methacryloyloxyethyl-2-trimethylammonioethyl phosphate, the constitutional unit represented by the formula (1b) comprises stearyl methacrylate, and the constitutional unit represented by the formula (1c) comprises 4-methacryloyloxybenzophenone.

5. A surface treatment agent, comprising the copolymer of claim 1.

6. A surface treatment agent according to claim 5, wherein the surface treatment agent comprises a surface treatment agent for suppressing protein adsorption.

7. A surface treatment agent according to claim 5, wherein the surface treatment agent comprises a surface treatment agent for suppressing cell adhesion.

8. A method of forming a crosslinked body, comprising:
   coating a substrate surface with the copolymer of claim 1; and
   then irradiating the substrate surface with light to form the crosslinked body on the substrate surface.

9. A crosslinked body, which is obtained by the method of forming a crosslinked body of claim 8.

10. A crosslinked body, which is obtained by irradiating the copolymer of claim 1 with light.

11. A crosslinked body, which is obtained by irradiating the surface treatment agent of claim 5 with light.

12. A medical device, comprising the crosslinked body of claim 10.

13. A medical device, comprising the crosslinked body of claim 11.

* * * * *